(12) United States Patent
Arimoto

(10) Patent No.: US 7,931,911 B2
(45) Date of Patent: Apr. 26, 2011

(54) PESTICIDAL/OVICIDAL COMPOSITION AND PESTICIDAL/OVICIDAL METHOD

(75) Inventor: Yutaka Arimoto, Wako (JP)

(73) Assignee: Riken, Wako-Shi, Saitama (JP)

( * ) Notice: Subject to any disclaimer, the term of this patent is extended or adjusted under 35 U.S.C. 154(b) by 242 days.

(21) Appl. No.: 12/296,359

(22) PCT Filed: Apr. 9, 2007

(86) PCT No.: PCT/JP2007/057849
§ 371 (c)(1),
(2), (4) Date: Oct. 7, 2008

(87) PCT Pub. No.: WO2007/117002
PCT Pub. Date: Oct. 18, 2007

(65) Prior Publication Data
US 2009/0061028 A1    Mar. 5, 2009

(30) Foreign Application Priority Data

Apr. 7, 2006 (JP) .................. 2006-106728

(51) Int. Cl.
*A01N 25/32* (2006.01)
(52) U.S. Cl. ........ 424/406; 424/405; 514/546; 514/547; 514/549; 514/558; 514/560
(58) Field of Classification Search ........................ None
See application file for complete search history.

(56) References Cited

U.S. PATENT DOCUMENTS

| 6,294,578 B1 | 9/2001 | Arimoto |  |
| 2006/0165748 A1 * | 7/2006 | Arimoto | ............ 424/405 |

FOREIGN PATENT DOCUMENTS

| JP | 53-047532 A |   | 4/1978 |
| JP | 56-092207 A |   | 7/1981 |
| JP | 56-138105 A |   | 10/1981 |
| JP | 56-140911 A |   | 11/1981 |
| JP | 10-251104 A |   | 9/1998 |
| JP | 2005-029489 A |   | 2/2005 |
| WO | WO 2005/087195 | * | 9/2005 |
| WO | WO 2006/028170 A1 |   | 3/2006 |

OTHER PUBLICATIONS

International Search Report for corresponding application No. PCT/JP2007/057849, completed Apr. 23, 2007.
Written Opinion for corresponding application No. PCT/JP2007/057849, completed Apr. 23, 2007 (in Japanese).

* cited by examiner

*Primary Examiner* — Neil Levy
(74) *Attorney, Agent, or Firm* — Buchanan Ingersoll & Rooney PC

(57) ABSTRACT

A pesticidal/ovicidal composition comprising: (a) 50-97.9 parts by mass of a triglyceride containing not less than 50% of oleic acid as a fatty acid component; (b) 0.1-20 parts by mass of a cationic surface active agent; and (c) 2-30 parts by mass of a glycerin derivative, and a pesticidal/ovicidal method using the same. The composition according to the invention has not only a pesticidal activity but also an ovicidal activity on crop pests, and provides a safe and high pesticidal/ovicidal effect.

7 Claims, No Drawings

PESTICIDAL/OVICIDAL COMPOSITION AND PESTICIDAL/OVICIDAL METHOD

TECHNICAL FIELD

The present invention relates to a pesticidal/ovicidal composition and a pesticidal/ovicidal method.

BACKGROUND ART

Various agents have been known as a fungicide and a triglyceride-based pesticidal composition against crop pests such as mites and aphids. For example, Patent Document 1 discloses a fungicidal composition comprising a phospholipid and an edible oil. Patent Documents 2 to 4 disclose a miticide comprising animal and vegetable oils and a surfactant. These Documents, however, do not disclose that the above compositions work on mite eggs.

Patent Document 5 discloses a triglyceride composed of unsaturated fatty acid, which shows high pesticidal and ovicidal effects by combining a coconut oil, a palm kernel oil, triglyceride composed of $C_{12}$ and $C_{14}$ fatty acids (mixing ratio: from 4:1 to 1:4), triglyceride composed of $C_{12}$ and $C_{18-1}$ fatty acids (mixing ratio: from 4:1 to 1:4), triglyceride composed of $C_{12}$, $C_{14}$ and $C_{18-1}$ fatty acids (mixing ratio: 1-4:1-4:1-4), triglyceride composed of $C_{10}$ and $C_{18-1}$ fatty acids (mixing ratio: from 4:1 to 1:4), trioleate, and DO-100 (diglycerol oleate) or DL-100 (diglycerol laurate) with a specific adjuvant. However, since glycerides other than the coconut oil and the palm kernel oil are synthetically produced, they require high production costs and are of little practical use.

Accordingly, in recent years, there is a demand for an agent, which is amenable to various applications, has no risk of drug resistance induction, and is safe for crops and natural environment-friendly.

Patent Document 1: JP-A-53-47532
Patent Document 2: JP-A-56-92207
Patent Document 3: JP-A-56-138105
Patent Document 4: JP-A-56-140911
Patent Document 5: JP-A-2005-29489

DISCLOSURE OF THE INVENTION

Problems To Be Solved by the Invention

Accordingly, an object of the invention is to provide a pesticidal/ovicidal composition which has not only a pesticidal effect but also an ovicidal effect on crop pests.

Another object of the invention is to provide a pesticidal/ovicidal method against crop pests.

Means to Solve the Problems

The present invention has been completed based on a finding that fats and oils having a particular fatty acid composition display excellent pesticidal/ovicidal effects on imagines, larvae and eggs of crop pests. The invention provides pesticidal/ovicidal compositions and pesticidal/ovicidal methods as described below 1. A pesticidal/ovicidal composition comprising.
(a) 50-97.9 parts by mass of a triglyceride containing not less than 50% of oleic acid as a fatty acid component,
(b) 0.1-20 parts by mass of a cationic surface active agent; and
(c) 2-30 parts by mass of a glycerin derivative.
2. The pesticidal/ovicidal composition according to above item 1, wherein said cationic surface active agent is at least one selected from the group consisting of amines, amine salts and quaternary ammonium salts.
3. The pesticidal/ovicidal composition according to above item 1, wherein said cationic surface active agent is at least one selected from the group consisting of aliphatic amines, amine salts and quaternary ammonium salts.
4. The pesticidal/ovicidal composition according to above item 1, wherein said cationic surface active agent is at least one selected from the group consisting of lauryl dihydroxyethyl amine, hexadecyl amine, hexadecyl hydroxyethyl amine, lauryl amine acetate, hexadecyl poly (15) hydroxy ethyl amine, lauryl dimethyl benzalkonium chloride, oleyl dihydroxyethyl methyl ammonium chloride, and octadecyl dimethyl benzalkonium.
5. The pesticidal/ovicidal composition according to any one of above items 1 to 4, further comprising:
(d) a vegetable oil in an amount not more than 39 parts by mass,
relative to 100 parts by mass of the total amount of the components (a), (b) and (c).
6. The pesticidal/ovicidal composition according to any one of above items 1 to 5, which is diluted by 100-fold to 1000-fold with water.
7. A pesticidal/ovicidal method which comprises the step of spraying to crops the pesticidal/ovicidal composition according to any one of above items 1 to 6, in such an amount that the total amount of the components (a), (b) and (c) is in the range between 0.2 kg/10a and 8 kg/10a.
8. The pesticidal/ovicidal method according to above item 7 which comprises the step of spraying to crops the pesticidal/ovicidal composition, in such an amount that the total amount of the components (a), (b) and (c) is in the range between 0.5 kg/10a and 3 kg/10a.

EFFECTS OF THE INVENTION

Since the pesticidal/ovicidal composition according to the invention employs triglyceride, which is used in food, as a main ingredient, it has no stress on human bodies and natural environments and no risk of drug resistance induction, and shows pesticidal and ovicidal effects even on crop pests which already have acquired resistances to other drugs. In addition, the composition according to the invention displays sufficient pesticidal and ovicidal effects even at lower concentrations.

BEST MODES FOR CARRYING OUT THE INVENTION

The triglyceride component (a) used for the composition of the invention contains oleic acid as a constituent fatty acid in an amount not less than 50%, preferably, not less than 55%, and more preferably, not less than 60% by mass. Examples of such triglyceride include olive oil (containing oleic acid in an amount of 60-80% by mass), extra virgin olive oil (60-80% by mass), camellia oil (about 85% by mass), almond oil (60-70% by mass), avocado oil (64-94% by mass), tea seed oil (about 88% by mass), safflower oil (high oleic acid variety) (70-80% by mass), sunflower oil (high oleic acid variety) (75-80% by mass), and oils from other high oleic acid plants. Among these, sunflower oil (high oleic acid variety), safflower oil (high oleic acid variety) and extra virgin olive oil are preferred.

The composition according to the invention contains component (a) in an amount of 50-97.9 parts by mass, preferably, 70-97.9 parts by mass, and more preferably, 80-97.9 parts by mass, relative to 100 parts by mass of the total amount of the components (a), (b) and (c) Triglyceride content of 50-97.9 parts by mass is preferable for the composition of the invention, because triglyceride content in such range tends to exert pesticidal/ovicidal effect.

For the composition of the invention, an adjuvant containing components (b) and (c) is used.

Adjuvant component (b) is a cationic surface active agent. Examples of such a cationic surface active agent include at least one selected from the group consisting of amines, amine salts and quaternary ammonium salts. Specific examples include lauryl dihydroxyethyl amine, hexadecyl amine, hexadecyl hydroxyethyl amine, lauryl amine acetate, hexadecyl poly (15) hydroxy ethyl amine, lauryl dimethyl benzalkonium chloride, oleyl dihydroxyethyl methyl ammonium chloride, and octadecyl dimethyl benzalkonium.

The pesticidal/ovicidal composition of the invention contains component (b) in an amount of 0.1-20 parts by mass, preferably, 0.1-10 parts by mass, and more preferably, 0.5-5 parts by mass, relative to 100 parts by mass of the total amount of the components (a), (b) and (c).

Preferably, the pesticidal/ovicidal composition of the invention further includes a glycerin derivative as adjuvant component (c). Examples of the glycerin derivative for component (c) include monoglycerol fatty acid esters and polyglycerol fatty acid esters. More specifically, glycerol monoalkyl fatty acid esters, glycerol dialkyl fatty acid esters, polyglycerol monoalkyl fatty acid esters and polyglycerol polyalkyl fatty acid esters are included. Among these, polyglycerol fatty acid esters are preferable, and diglycerol fatty acid esters are more preferable. Preferably, constituent fatty acids for such esters are $C_{12}$-$C_{18}$ fatty acids, such as oleic acid and lauric acid.

The pesticidal/ovicidal composition of the invention contains component (c) in an amount of 2-30 parts by mass, preferably, 2-20 parts by mass, and more preferably, 2-10 parts by mass, relative to 100 parts by mass of the total amount of the components (a), (b) and (c).

The pesticidal/ovicidal composition of the invention may optionally include, as component (d), a vegetable oil other than component (a). Examples of such vegetable oil include sesame oil, safflower oil, soybean oil, corn oil, sunflower oil and cottonseed oil. Among these, safflower oil, soybean oil, corn oil, sunflower oil and cottonseed oil are preferable, and soybean oil and cottonseed oil are more preferable.

The pesticidal/ovicidal composition of the invention may contain the component (d) in an amount not more than 39 parts by mass, preferably, not more than 20 parts by mass, and more preferably, not more than 15 parts by mass, relative to 100 parts by mass of the total amount of the components (a), (b) and (c). Use of a vegetable oil other than (a) as component (d) broadens the spectrum of the targets of ovicidal effect. In order to achieve this, it is preferable to use not less than 5 parts by mass.

The pesticidal/ovicidal composition of the present invention is preferably sprayed after dilution with water by preferably 100-fold to 1000-fold, more preferably 200-fold to 500-fold, so as to attain a total concentration of the active ingredients of preferably about 0.1 to 1% by mass, more preferably about 0.2 to 0.5% by mass.

It is preferable to spray, to crops, the pesticidal/ovicidal composition of the invention, in such an amount that the total amount of components (a), (b) and (c) is in the range between 0.2% kg/10a and 8 kg/10a, more preferably, in the range between 0.5 kg/10a and 3 kg/10a.

In general, the pesticidal/ovicidal composition of the invention can be applied from the initial phase to terminal phase of oviposition, however, the term for application depends on types of vermin pests. Although earlier application provides higher efficiency, the composition of the invention would work when applied even after laid eggs are identified due to its high ovicidal activity.

The pesticidal/ovicidal composition of the invention has a pesticidal effect on any agricultural vermin pests, and ovicidal effect on eggs thereof. Examples of the subject vermin pests include:

Lepidopteras: *Mamestra brassicae*, *Leucania separata* and *Plutella maculipennis*;
Tetranychidae: *Panonychus citri*, *Tetranychus urticae* and *Tetranychus kanzawai*;
Eriophyidae: *Aculus pelekassi* and *Aculops lycopersici*;
Tarsonemidae: *Brevipalpus obovatus*;
Astigmatae: *Tyrophagus similes*;
Aphidoideae: *Aphis gossypii*, *Myzus persicae* and *Aulacorthum solani*;
Hemipterae: *Trialeurodes vaporariorus* and *Bemisia tabaci*; and
Coccoideae: *Icerya purchasi*, *Unaspis yanonensis* and *Ceroplastes pseudoceriferus*.

EXAMPLES

The present invention will be explained more in detail by way of referring to Examples, Comparative Examples and Experimental Examples described below. However, these examples are not intended to limit the scope of the invention.

Components (b) and (c) for pesticidal/ovicidal composition used in Examples and Comparative Examples below (hereinafter, an adjuvant containing both of these components will be referred to as "Adjuvant B") are as follows.

Adjuvant B1

Adjuvant B1 is a mixture of diglycerol monooleate and lauryl dihydroxyethyl amine at a ratio of 9:1. Examples of diglycerol monooleate include Rikemal DO-100 (a product from Riken Vitamin Co, Ltd., Japan), Examples of lauryl dihydroxyethyl amine include Solpole 7643 (a product from Toho Chemical Industry Co., Ltd, Japan).

Adjuvant B2

Adjuvant B2 is a mixture of diglycerol monooleate and oleyl dihydroxyethyl methyl ammonium chloride at a ratio of 3:1. Examples of diglycerol monooleate include Rikemal DO-100 (a product from Riken Vitamin Co., Ltd., Japan) Examples of oleyl dihydroxyethyl methyl ammonium chloride include Solpole EX-49 (a product from Toho Chemical Industry Co., Ltd., Japan).

Adjuvant B3

Adjuvant B3 is a mixture of diglycerol monooleate and octadecyl dimethyl benzalkonium at a ratio of 3:1. Examples of diglycerol monooleate include Rikemal DO-100 (a product from Riken Vitamin Co., Ltd., Japan). Examples of octadecyl dimethyl benzalkonium include Solpole EX-48 (a product from Toho Chemical Industry Co., Ltd., Japan).

Adjuvant B4

Adjuvant B4 is a mixture of Actor M-1, Rikemal B205 and Rikemal O-71-D (all of these are products from Riken Vitamin Co., Ltd, Japan) at a ratio of 1:1:1.

Adjuvant B5

Adjuvant B5 is a mixture of soybean oil, Solpole 355H and AG-7520 at a ratio of 1:1:1.

Actor M-1: tricaprylin (70% by mass)/tricaprin (30% by mass)

Rikemal B205: polyoxyethylene lauryl ether

Rikemal O-71-D: diglycerol oleate (one selected from the group of monooleate to hexaoleate, or a mixture thereof)

Solpole 355H: (a mixture of Solpole T-20, Solpole T-26, Solpole EX-15 and alkylbenzene)
Solpole T-20: polyoxyethylene styryl phenyl ether (HLB13.3)
Solpole T-26: polyoxyethylene styryl phenyl ether (HLB14.4)
Solpole EX-15: alkyl allyl sulfonate calcium
Alkylbenzene
AG-7520: polyglycerol oleate (a product from Riken Vitamin Co., Ltd., Japan)
Solpole 4105: emulsifier for vegetable oils (mixture)

Solpole is a product name owned by Toho Chemical Industry Co., Ltd., Japan, while Rikemal and Actor are product names owned by Riken Vitamin Co., Ltd., Japan.

Example 1

Oleic acid-rich sunflower oil (oleic acid: about 80%) and Adjuvant B1 were mixed at a ratio of 80:20 to produce Formulation 1.

Example 2

Oleic acid-rich safflower oil (oleic acid: about 80%) and Adjuvant B2 were mixed at a ratio of 80:20 to produce Formulation 2.

Example 3

Extra virgin olive oil (oleic acid: about 80%) and Adjuvant B3 were mixed at a ratio of 80:20 to produce Formulation 3.

Example 4

Triolein (oleic acid: 100%) and Adjuvant B3 were mixed at a ratio of 80:20 to produce Formulation 4.

Comparative Example 1

Comparative Formulation 1 contained Adjuvant B1 only.

Comparative Example 2

Cottonseed oil (oleic acid: about 20%) and Adjuvant B2 were mixed at a ratio of 80:20 to produce Comparative Formulation 2

Comparative Example 3

Sunflower oil (oleic acid: about 20%) and Adjuvant B3 were mixed at a ratio of 80:20 to produce Comparative Formulation 3.

Comparative Example 4

Oleic acid-rich safflower oil (oleic acid: about 80%) and Solpole 4105 (a common emulsifier for fats and oils) were mixed at a ratio of 95:5 to produce Comparative Formulation 4.

Comparative Example 5

Oleic acid-rich sunflower oil (oleic acid: 80%) and Adjuvant B4 were mixed at a ratio of 80:20 to produce Comparative Formulation 5.

Comparative Example 6

Extra virgin olive oil (oleic acid: about 80%) and Adjuvant B5 were mixed at a ratio of 80:20 to produce Comparative Formulation 6.

Experimental Example 1

Effect on *Tetranychus urticae* Koch

Formulations 1-4 and Comparative Formulations 1, 4-6 were examined for their pesticidal/ovicidal effects on eggs of *Tetranychus urticae* Koch. In brief, leaf discs for *Tetranychus urticae* Koch growth were cut out of snap bean leaves, on which *Tetranychus urticae* Koch had preliminarily been grown, and then left in a snap bean seedling pot for three days to allow *Tetranychus urticae* Koch to oviposit, followed by spraying each of the formulations (concentration: 300 mg/100 ml) diluted by 300-fold with water using a spray gun. Then, the snap bean pot was placed in a glass green house to grow *Tetranychus urticae* Koch. Hatchings were checked daily and ovicidal efficiency was calculated. The preventive value was calculated based on the number of female imagines of *Tetranychus urticae* Koch 14 days after spraying.

(%) Efficiency of killing eggs=(1−the number of hatched eggs/the total number of eggs)×100

(%) Preventive value=100−(%) corrected density index (%) corrected density index=$(A_1/A_0) \times (B_0/B_1) \times 100$ $A_0$: The number of female imagines of *Tetranychus urticae* Koch before treatment in treatment area
$A_1$: The number of female imagines of Tetranychus urticae Koch 14 days after treatment in treatment area
$B_0$: The number of female imagines of *Tetranychus urticae* Koch before treatment in non-treatment area
$B_1$: The number of female imagines of *Tetranychus urticae* Koch 14 days after treatment in non-treatment area

Experimental Example 2

Effect on *Polyphagotarsonemus latus*

Formulations 1-4 and Comparative Formulations 1, 4-6 were examined for their pesticidal/ovicidal effects on *Polyphagotarsonemus latus* on eggplant. In brief, each of the formulations (concentration: 300 mg/100 ml) diluted by 300-fold with water was sprayed using a spray gun to eggplant seedlings (variety: Senryou No. 2, leaf stage: 5-6, the number of seedlings per area: 3), which showed decreased growth due to a damage by *Polyphagotarsonemus latus*. Then, the eggplant seedlings were placed in a glass green house to grow. The damage extent of newly developing leaf was checked and preventive value was calculated. The damage extent was classified as follows and the preventive value was calculated based on the following equation. Total extent of damage (total for three seedlings) in each area was determined based on following criteria.
No damage: 0, Scarce damage: 20,
Moderate damage: 70, Serious damage: 100

(%) Preventive value=(1−damage extent in treatment area/damage extent in non-treatment area)×100

Experimental Example 3

Pesticidal/Ovicidal Effect on *Aculops lycopersici*

Formulations 1-4 and Comparative Formulations 1, 4-6 were examined for their pesticidal/ovicidal effects on *Acu-*

*lops lycopersici*. In brief, *Aculops lycopersici* were released onto tomato seedlings (variety: Momotaro, leaf stage: 8, the number of seedlings per area: 3), and the seedlings were placed in a glass green house to grow. After confirming disease development, each of the formulations (concentration: 300 mg/100 ml) diluted by 300-fold with water was sprayed using a spray gun. The seedlings were allowed to grow further, and then the extent of damage spread was checked and preventive value was calculated based on the following equation. The extent of damage spread was classified as follows. Total extent of damage spread (total of three seedlings) in each area was determined based on the following criteria.

No damage spread: 0, Slight damage spread: 20,
Medium damage spread: 70, Serious damage spread: 100

(%) Preventive value=(1−(the extent of damage spread in treatment area)/(the extent of damage spread in non-treatment area))×100

The results of Experimental Examples 1-3 are shown in Table 1.

TABLE 1

| | Pesticidal/ovicidal effects (%) | | | |
|---|---|---|---|---|
| | *Tetranychus urticae* Koch | | *Polyphagotarsonemus* | *Aculops* |
| Sample | Imagines | Eggs | *latus* | *lycopersici* |
| Example 1 | 100 | 99 | 94 | 92 |
| Example 2 | 100 | 98 | 94 | 91 |
| Example 3 | 100 | 99 | 100 | 98 |
| Example 4 | 78 | 42 | 67 | 87 |
| Comparative Example 1 | 0 | 0 | 0 | 0 |
| Comparative Example 4 | 22 | 35 | 20 | 7 |
| Comparative Example 5 | 25 | 33 | 20 | 11 |
| Comparative Example 6 | 28 | 41 | 10 | 3 |
| Non-treatment | 0 | 0 | 0 | 0 |

Experimental Example 4

Effect on *Trialeurodes vaporariorum* Westwood

Effect on Eggs

Imagines of *Trialeurodes vaporariorum* Westwood were released onto cucumber leaves and allowed to oviposit for two days, followed by spraying each of the formulations being diluted to the prescribed concentration Then, the leaves were incubated in a glass green house, and the number of larvae of *Trialeurodes vaporariorum* alive were counted 14 days after spraying.

(%) Ovicidal efficiency=(the number of unhatched eggs/the total number of eggs)×100

Effect on Larvae

Each of the formulations diluted to the prescribed concentration was sprayed to cucumber leaves on which third to forth-instar larvae were alive. Then, the leaves were incubated in a glass green house, and survival of the larvae of *Trialeurodes vaporariorum* were judged by microscopy and the number of death was counted 4 days after spraying.

(%) Pesticidal efficiency=(the number of dead larvae/ the total number of larvae)×100

Experimental Example 5

Effect on *Aphis gossypii* Glover

Each of the formulations diluted to the prescribed concentration was sprayed to the *Aphis gossypii* Glover alive on the back sides of cucumber true leaves. Then, the leaves were incubated in a glass green house, and survival of the larvae of *Aphis gossypii* Glover were judged and the number of death was counted 4 days after spraying.

(%) Pesticidal efficiency=(the number of dead larvae/ the total number of larvae)×100

Experimental Example 6

Effect on *Pseudococcus comstocki* Kuwana

Eggs of *Pseudococcus comstocki* Kuwana cultured on pumpkin were attached to snap bean leaves, followed by spraying each of the formulations diluted by 300-fold with water using a spray gun. Then, the leaves were allowed to continue growing in a green house, and the state and ratio of hatching were examined.

Each of the formulations diluted by 300-fold with water was sprayed to the larvae after hatching using a spray gun. The larvae were checked through time courses and the pesticidal efficiency was calculated.

(%) Ovicidal efficiency=(the number of unhatched eggs/the total number of eggs)×100

(%) Pesticidal efficiency=(the number of dead larvae/ the total number of larvae)×100

Pesticidal/ovicidal effects of each formulation on pests are shown in Table 2.

TABLE 2

| | Pesticidal/ovicidal effects (%) | | | | |
|---|---|---|---|---|---|
| | *Trialeurodes vaporariorum* Westwood | | *Aphis gossypii* | *Pseudococcus comstocki* Kuwana | |
| Sample | Larvae | Eggs | Glover | Larvae | Eggs |
| Example 1 | 100 | 82 | 100 | 100 | 82 |
| Example 2 | 100 | 84 | 100 | 100 | 86 |
| Example 3 | 98 | 85 | 98 | 96 | 92 |
| Example 4 | 66 | 34 | 58 | 78 | 37 |
| Comparative Example 1 | 0 | 0 | 0 | 0 | 0 |
| Comparative Example 4 | 13 | 8 | 22 | 8 | 5 |
| Comparative Example 5 | 21 | 10 | 24 | 12 | 6 |
| Comparative Example 6 | 17 | 14 | 23 | 16 | 5 |
| Non-treatment | 0 | 0 | 0 | 0 | 0 |

Experimental Example 7

Effect on *Tetranychus urticae* Koch

Effects on *Tetranychus urticae* Koch were examined in the same manner as described in Experimental Example 1 except that each of the formulations (concentration: 125 mg/100 ml) was diluted by 800-fold with water for use. The results are shown in Table 3.

TABLE 3

| Sample | Pesticidal/ovicidal effects (%) | |
| --- | --- | --- |
|  | Imagines | Eggs |
| Example 1 | 97 | 78 |
| Example 2 | 96 | 75 |
| Example 3 | 99 | 80 |
| Example 4 | 52 | 18 |
| Comparative Example 1 | 0 | 0 |
| Comparative Example 4 | 20 | 8 |
| Comparative Example 5 | 18 | 5 |
| Comparative Example 6 | 21 | 11 |
| Non-treatment | 0 | 0 |

Since the pesticidal/ovicidal composition according to the invention is prepared from food products and food additives as main ingredients, it has no stress on human bodies and natural environments and no risk of drug resistance induction, and can be applied to even pests which already have acquired resistances to other drugs. In addition, the composition according to the invention can be used at lower concentrations as compared to conventional methods. Furthermore, due to its excellent ovicidal effect, the composition can provide an increased preventive effect on a variety of crop pests per spray as compared to conventional pesticides.

What is claimed is:

1. A pesticidal/ovicidal composition comprising:
   (a) 50-97.9 parts by mass of a triglyceride containing not less than 50% of oleic acid as a fatty acid component;
   (b) 0.1-20 parts by mass of a cationic surface active agent; and
   (c) 2-30 parts by mass of a glycerin derivative,
   relative to 100 parts by mass of the total amount of components (a), (b), and (c),
   wherein said cationic surface active agent is at least one agent selected from the group consisting of lauryl dihydroxyethyl amine, hexadecyl amine, hexadecyl hydroxyethyl amine, lauryl amine acetate, hexadecyl poly (15) hydroxy ethyl amine, lauryl dimethyl benzalkonium chloride, oleyl dihydroxyethyl methyl ammonium chloride, and octadecyl dimethyl benzalkonium; and
   further wherein said glycerin derivative is at least one derivative selected from the group consisting of glycerol monoalkyl fatty acid esters, glycerol dialkyl fatty acid esters, polyglycerol monoalkyl fatty acid esters, and polyglycerol polyalkyl fatty acid esters, wherein said fatty acid esters have $C_{12}$-$C_{18}$ fatty acids.

2. The pesticidal/ovicidal composition according to claim 1, further comprising:
   (d) a vegetable oil in an amount not more than 39 parts by mass, relative to 100 parts by mass of the total amount of the components (a), (b), and (c).

3. The pesticidal/ovicidal composition according to claim 1, which is diluted by 100-fold to 1000-fold with water.

4. The pesticidal/ovicidal composition according to claim 1, wherein said cationic surface active agent is at least one agent selected from the group consisting of lauryl dihydroxyethyl amineoleyl, dihydroxyethyl methyl ammonium chloride, and octadecyl dimethyl benzalkonium.

5. The pesticidal/ovicidal composition according to claim 1, wherein said glycerin derivative is a polyglycerol monoalkyl fatty acid ester and wherein said fatty acid esters have $C_{12}$-$C_{18}$ fatty acids.

6. A pesticidal/ovicidal method which comprises spraying onto a crop the pesticidal/ovicidal composition according to claim 1, in such an amount that the total amount of the components (a), (b), and (c) is in the range between 0.2 kg/10a and 8 kg/10a.

7. The pesticidal/ovicidal method according to claim 6, which comprises spraying onto a crop the pesticidal/ovicidal composition, in such an amount that the total amount of the components (a), (b), and (c) is in the range between 0.5 kg/10a and 3 kg/10a.

* * * * *